United States Patent
Dementyev et al.

(10) Patent No.: US 10,295,631 B2
(45) Date of Patent: May 21, 2019

(54) COMPOSITE NOISE SHIELD FOR MAGNETIC RESONANCE TOOLS

(71) Applicant: Schlumberger Technology Corporation, Sugar Land, TX (US)

(72) Inventors: Anatoly Dementyev, Sugar Land, TX (US); Krishnamurthy Ganesan, Sugar Land, TX (US); Gabriela Leu, Richmond, TX (US); Nicholas Heaton, Sugar Land, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 141 days.

(21) Appl. No.: 15/143,311

(22) Filed: Apr. 29, 2016

(65) Prior Publication Data

US 2017/0315189 A1 Nov. 2, 2017

(51) Int. Cl.
*G01R 33/422* (2006.01)
*G01V 3/32* (2006.01)
*G01N 24/08* (2006.01)

(52) U.S. Cl.
CPC ......... *G01R 33/422* (2013.01); *G01N 24/081* (2013.01); *G01V 3/32* (2013.01)

(58) Field of Classification Search
CPC ......... G01R 33/422; G01N 24/81; G01V 3/32
See application file for complete search history.

(56) References Cited

U.S. PATENT DOCUMENTS

| 6,111,410 | A  | * | 8/2000 | Young | G01R 33/3806 324/309 |
| 6,172,587 | B1 | * | 1/2001 | Schmidt | G01R 33/421 335/296 |
| 6,174,001 | B1 |   | 1/2001 | Enderle | |
| 6,268,726 | B1 | * | 7/2001 | Prammer | G01N 24/081 324/300 |
| 2004/0055745 | A1 | * | 3/2004 | Georgi | E21B 49/00 166/250.02 |
| 2004/0066194 | A1 | * | 4/2004 | Slade | G01R 33/3808 324/318 |
| 2006/0192554 | A1 | * | 8/2006 | Blanz | E21B 49/00 324/303 |
| 2008/0060843 | A1 | * | 3/2008 | Ginanneschi | G01R 33/422 174/378 |
| 2008/0150524 | A1 | * | 6/2008 | Song | G01N 24/081 324/303 |

(Continued)

OTHER PUBLICATIONS

Bunn, G. F. et al., "Design, Implementation, and Interpretation of a Three-Dimensional Well Test in the Cormorant Field, North Sea", SPE 15858, presented at the SPE European Petroleum Conference held in London, UK, 1986, 10 pages.

(Continued)

*Primary Examiner* — Tung X Nguyen
*Assistant Examiner* — Dominic E Hawkins

(57) ABSTRACT

An arrangement for shielding an NMR tool from electromagnetic noise, having a nuclear magnetic resonance tool configured to send and receive signals, a first shield configured around a nuclear magnetic resonance antenna of the nuclear magnetic resonance tool and a second shield configured to reduce the effects of eddy currents in the first shield.

11 Claims, 6 Drawing Sheets
(6 of 6 Drawing Sheet(s) Filed in Color)

(56) References Cited

U.S. PATENT DOCUMENTS

| | | | |
|---|---|---|---|
| 2014/0285201 A1* | 9/2014 | Freytag | G01R 33/4215 |
| | | | 324/322 |
| 2016/0036494 A1* | 2/2016 | Dobyns | H04K 3/42 |
| | | | 455/41.1 |
| 2016/0124062 A1* | 5/2016 | Taicher | G01N 24/08 |
| | | | 324/309 |

OTHER PUBLICATIONS

Bunn, G. F. et al., "Distributed Pressure Measurements Allow Early Quantification of Reservoir Dynamics in the Jene Field", SPE 17682, SPE Formation Evaluation, 1991, pp. 55-62.

Kaneda, R., et al., "Interpretation of a Pulse Test in a Layered Reservoir", SPE 21337, SPE Formation Evaluation, 1991, pp. 453-462.

Lasseter, T. et al., "Interpreting an RFT-Measured Pulse Test with a Three-Dimensional Simulator", SPE 14878, SPE Formation Evaluation, 1988, pp. 139-146.

Saeedi, J. et al., "Layer Pulse Testing Using a Wireline Formation Tester", SPE 16803, presented at the 62nd Annual Technical Conference and Exhibition of the Society of Petroleum Engineers held in Dallas, Texas, USA, 1987, pp. 543-550.

Yaxley, L. M., et al., "A Field Example of Interference Testing Across a Partially Communicating Fault", SPE 19306, 1989, 41 pages.

\* cited by examiner

COMPOSITE NOISE SHIELD FOR MAGNETIC RESONANCE TOOLS

CROSS-REFERENCE TO RELATED APPLICATIONS

None.

FIELD OF THE INVENTION

Aspects relate to production of hydrocarbons from geological formations. More specifically, aspects relate to a composite noise shield for magnetic resonance tools to aid those tools in identification of hydrocarbons in the geological formations.

BACKGROUND INFORMATION

The production of hydrocarbons from geological stratum is an important part of modern economic development. Many different types of tools may be used to identify and retrieve these hydrocarbon materials from the geological stratum. Devices range from simple mechanical tools, such as drill bits, drill pipe and derricks to more complicated devices, such as nuclear magnetic resonance tools.

The more complex the tool, generally, the more potential sources of problems may be encountered. For some of the most complex tools, such as nuclear magnetic resonance tools, the complex machinery and devices that are used make the device prone to erroneous readings.

For nuclear magnetic resonance tools, different signals may be received by the circuitry and sensors or may be present or induced in the tool that may make the tool prone to erroneous readings. Typically, nuclear magnetic resonance tools require a conductive shield around the antenna to eliminate electromagnetic noise from environment, for example, to make accurate calibration measurements. Eddy currents induced in the shield boost the magnetic field created by the tool at the diameter of investigation. This, in turn, increases the nuclear magnetic resonance signal of the tool during the calibration measurements. The above-described shield effect introduces an error during the calibration measurements and thus degrades the desired porosity measurement accuracy if not properly corrected. One way to reduce to the shield eddy current effect is to use a really big 8' long shield. This big shield occupies a lot of space in the lab.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one example embodiment, an arrangement for shielding an NMR tool from electromagnetic noise is disclosed having a nuclear magnetic resonance tool configured to send and receive signals, a first shield configured around a nuclear magnetic resonance antenna of the nuclear magnetic resonance tool and a second shield configured to reduce the effects of eddy currents in the first shield. This new shield may be small and can be used in any lab/shop setup.

In a further example embodiment, an arrangement for shielding an electromagnetic noise in a downhole tool is described as having a nuclear magnetic resonance tool configured to send and receive signals to and from a calibration water tank, the tool having a body configured to house components, a first shield configured around a nuclear magnetic resonance antenna of the nuclear magnetic resonance tool, a second shield configured to eliminate eddy currents in the first shield, wherein the second shield is constructed from a ferrite film that is in contact with the first shield.

In a still further example embodiment, an arrangement for shielding an electromagnetic noise in a downhole tool is described as having a nuclear magnetic resonance tool configured to send and receive signals into a calibration water tank, the tool having a body configured to house components, a first shield configured around a nuclear magnetic resonance antenna of the nuclear magnetic resonance tool, and a second shield configured to eliminate eddy currents in the first shield, wherein the second shield is constructed from a ferrite film that is in contact with the first shield.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the drawings, sizes, shapes, and relative positions of elements are not drawn to scale. For example, the shapes of various elements and angles are not drawn to scale, and some of these elements may have been arbitrarily enlarged and positioned to improve drawing legibility.

FIG. 7 is a side elevation of a well site system used for establishing a wellbore in a geological stratum in which a nuclear magnetic resonance tool may be used.

DETAILED DESCRIPTION

Figure 1:
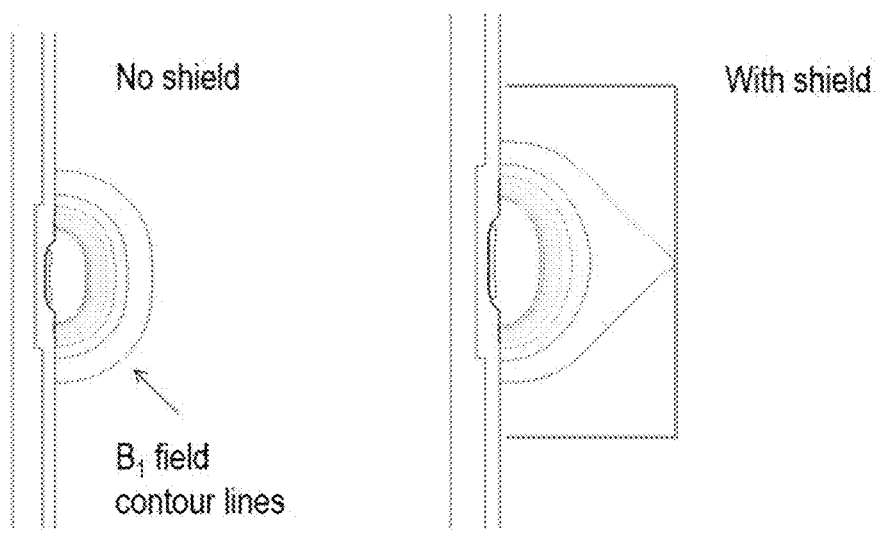
FIG. 1 is a side elevation of a B1 magnetic field contour lines from the antenna of a nuclear magnetic resonance tool with and without a calibration shield in place.

An example well site system is schematically depicted in FIG. 7. The well site comprises a well 110. A drill string 105 may extend from the drill rig 101 into a zone of the formation of reservoir 115. The drill string 105 uses a mud pulse telemetry system 100, described later, for transmitting data to and from downhole to the surface.

The drill string 105 may also use any type of telemetry system or any combination of telemetry systems, such as electromagnetic, mud pulse, acoustic and\or wired drill pipe, however in the illustrated embodiment, only the mud pulse telemetry system is used. A bottom hole assembly is suspended at the end of the drill string 105. In an embodiment, the bottom hole assembly comprises a plurality of measurement while drilling or logging while drilling downhole tools 125, such as a nuclear magnetic resonance tool such as shown by numerals 6a and 6b.

Logging while drilling tools used at the end of the drill string 105 may include a thick walled housing, commonly referred to as a drill collar, and may include one or more of a number of logging devices. The logging while drilling tool may be capable of measuring, processing, and/or storing information therein, as well as communicating with equipment disposed at the surface of the well site.

Measurement while drilling tools may include one or more of the following measuring tools: a modulator, a weight on bit measuring device, a torque measuring device, a vibration measuring device, a shock measuring device, a stick-slip measuring device, a direction measuring device, and inclination measuring device, and\or any other device.

Measurements made by the bottom hole assembly or other tools and sensors with the drill string 105 may be transmitted to a surface computing system 185 for analysis. For example, mud pulses may be used to broadcast formation measurements performed by one or more of the downhole tools 6a and 6b to the surface computing system 185.

The surface computing system 185 is configured to host a plurality of models, such as a reservoir model, and to acquire and process data from downhole components, as well as determine the bottom hole location in the reservoir 115 from measurement while drilling data. Examples of reservoir models and cross well interference testing may be found in the following references: "Interpreting an RFT-Measured Pulse Test with a Three-Dimensional Simulator" by Lasseter, T., Karakas, M., and Schweitzer, J., SPE 14878, March 1988. "Design, Implementation, and Interpretation of a Three-Dimensional Well Test in the Cormorant Field, North Sea" by Bunn, G. F., and Yaxley, L. M., SPE 15858, October 1986. "Layer Pulse Testing Using a Wireline Formation Tester" by Saeedi, J., and Standen, E., SPE 16803, September 1987. "Distributed Pressure Measurements Allow Early Quantification of Reservoir Dynamics in the Jene Field" by Bunn, G. F., Wittman, M. J., Morgan, W. D., and Curnutt, R. C., SPE 17682, March 1991. "A Field Example of Interference Testing Across a Partially Communicating Fault" by Yaxley, L. M., and Blaymires, J. M., SPE 19306, 1989. "Interpretation of a Pulse Test in a Layered Reservoir" by Kaneda, R., Saeedi, J., and Ayestaran, L. C., SPE 19306, December 1991.

The derrick or similar looking/functioning device, such as the drill rig 101 may be used to move the drill string 105 within the well that is being drilled through subterranean formations of the reservoir. The drill string 105 may be extended into the subterranean formations with a number of coupled drill pipes (one of which is designated 120) of the drill string 105. The drill pipe comprising the drill string 105 may be structurally similar to ordinary drill pipes, as illustrated for example and U.S. Pat. No. 6,174,001, issued to Enderle, entitled "Two-Step, a Low Torque, Wedge Thread for Tubular Connector," issued Aug. 7, 2001, which is incorporated herein by reference in its entirety, and includes a cable associated with each drill pipe 120 that serves as a communication channel.

The bottom hole assembly at the lower end of the drill string 105 may include one, an assembly, or a string of downhole tools. In the illustrated example, the downhole tool string 105 may include well logging tools 125 coupled to a lower end thereof. As used in the present description, the term well logging tool or a string of such tools, may include at least one or more logging while drilling tools ("LWD"), formation evaluation tools, formation sampling tools and other tools capable of measuring a characteristic of the subterranean formations of the reservoir 115 and\or of the well 110.

Several of the components disposed proximate to the drill rig 101 may be used to operate components of the system. These components will be explained with respect to their uses in drilling the well 110 for a better understanding thereof. The drill string 105 may be used to turn and actually urge a drill bit into the bottom the well 110 to increase its length (depth). During drilling of the well 110, a pump 130 lifts drilling fluid (mud) 135 from a tank 140 or pits and discharges the mud 135 under pressure through a standpipe 145 and flexible conduit 150 or hose, through a top drive 155 and into an interior passage inside the drill pipe 105. The mud 135 which can be water or oil-based, exits the drill pipe 105 through courses or nozzles (not shown separately) in the drill bit 116, wherein the mud 135 cools and lubricates the drill bit 116 and lifts drill cuttings generated by the drill bit 116 to the surface of the earth through an annular arrangement.

When the well 110 has been drilled to a selected depth, the well logging tools 125 may be positioned at the lower end of the pipe 105 if not previously installed. The well logging tools 125 may be positioned by pumping the well logging tools 125 down the pipe 105 or otherwise moving the well logging tools 125 down the pipe 105 while the pipe 105 is within the well 110. The well logging tools 125 may then be coupled to an adapter sub 160 at the end of the drill string 105 and may be moved through, for example in the illustrated embodiment, a highly inclined portion 165 of the well 110, which would be inaccessible using armored electrical cable to move the well logging tools 125.

During well logging operations, the pump 130 may be operated to provide fluid flow to operate one or more turbines in the well logging tools 125 to provide power to operate certain devices in the well logging tools 125. When tripping in or out of the well 110, it may not be feasible to provide fluid flow. As a result, power may be provided to the well logging tools 125 in other ways. For example, batteries may be used to provide power to the well logging tools 125. In one embodiment, the batteries may be rechargeable batteries and may be recharged by turbines during fluid flow. The batteries may be positioned within the housing of one or more of the well logging tools 125. Other manners of powering the well logging tools 125 may be used including, but not limited to, one-time power use batteries.

As the well logging tools 125 are moved along the well 110 by moving the drill string 105, signals may be detected by various devices, of which non-limiting examples may include a resistivity measurement device, a bulk density measurement device, a porosity measurement device, a formation capture cross-section measurement device 170, a gamma ray measurement device 175 and a formation fluid sampling tool 610, 710, 810 which may include a formation pressure measurement device or nuclear magnetic resonance device 6a and/or 6b. The signals may be transmitted toward the surface of the earth along the drill string 105.

An apparatus and system for communicating from the drill pipe 105 to the surface computer 185 or other component configured to receive, analyze, and/or transmit data may include a second adapter sub 190 that may be coupled between an end of the drill string 105 and the top drive 155 that may be used to provide a communication channel with a receiving unit 195 for signals received from the well logging tools 125. The receiving unit 195 may be coupled to the surface computer 185 to provide a data path therebetween that may be a bidirectional data path.

Though not shown, the drill string 105 may alternatively be connected to a rotary table, via a kelly, and may suspend from a traveling block or hook, and additionally a rotary swivel. The rotary swivel may be suspended from the drilling rig 101 through the hook, and the kelly may be connected to the rotary swivel such that the kelly may rotate with respect to the rotary swivel. The kelly may be any mast that has a set of polygonal connections or splines on the outer surface type that mate to a kelly bushing such that actuation of the rotary table may rotate the kelly.

An upper end of the drill string 105 may be connected to the kelly, such as by threadingly reconnecting the drill string 105 to the kelly, and the rotary table may rotate the kelly, thereby rotating the drill string connected thereto. Other systems, such as a top drive may also be used, therefore the system illustrated should be considered non-limiting.

Although not shown, the drill string 105 may include one or more stabilizing collars. A stabilizing collar may be disposed within or connected to the drill string 105, in which the stabilizing collar may be used to engage and apply a force against the wall of the well 110. This may enable the stabilizing collar to prevent the drill pipe string 105 from deviating from the desired direction for the well 110. For example, during drilling, the drill string 105 may "wobble" within the well 110, thereby allowing the drill string 105 to deviate from the desired direction of the well 110. This wobble action may also be detrimental to the drill string 105, components disposed therein, and the drill bit 116 connected thereto. A stabilizing collar may be used to minimize, if not overcome altogether, the wobble action of the drill string 105, thereby possibly increasing the efficiency of the drilling performed at the well site and/or increasing the overall life of the components at the wellsite.

Nuclear magnetic resonance (NMR) tools, as illustrated in the drill string 105 above often require a noise shield for calibration measurements and for accurate field measurements. Eddy currents induced in the shield, boost the B1 magnetic field created by the tool at the diameter of investigation (DOI) of the tool (see FIGS. 1 and 2). This increases the NMR signal of the tool during the calibration measurements. The above-described shield effect introduces an error during the calibration measurements and thus degrades the porosity measurement accuracy if not properly corrected.

Figure 2:
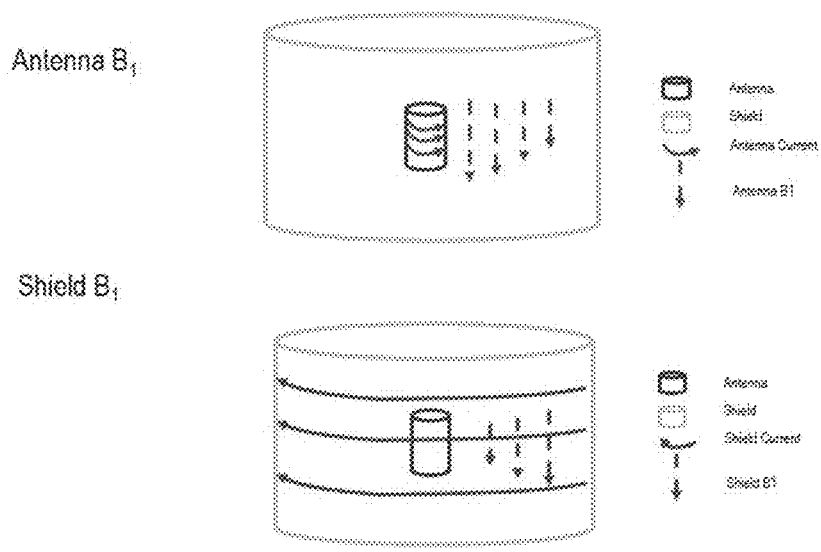
FIG. 2 is a side elevation of an arrangement illustrating the shield effect wherein eddy currents are induced in the shield that boost the magnetic field from the tool, thus increasing the nuclear magnetic field strength.

As evidence of these signals, FIG. 1 illustrates a B1 magnetic field from a nuclear magnetic resonance tool sensor that is affected by the calibration shield. Referring to FIG. 2, a diagram of the shield effect is illustrated. In FIG. 2, eddy currents induced in the shield boost the B1 magnetic field from the tool thus increasing the NMR signal.

Figure 3:
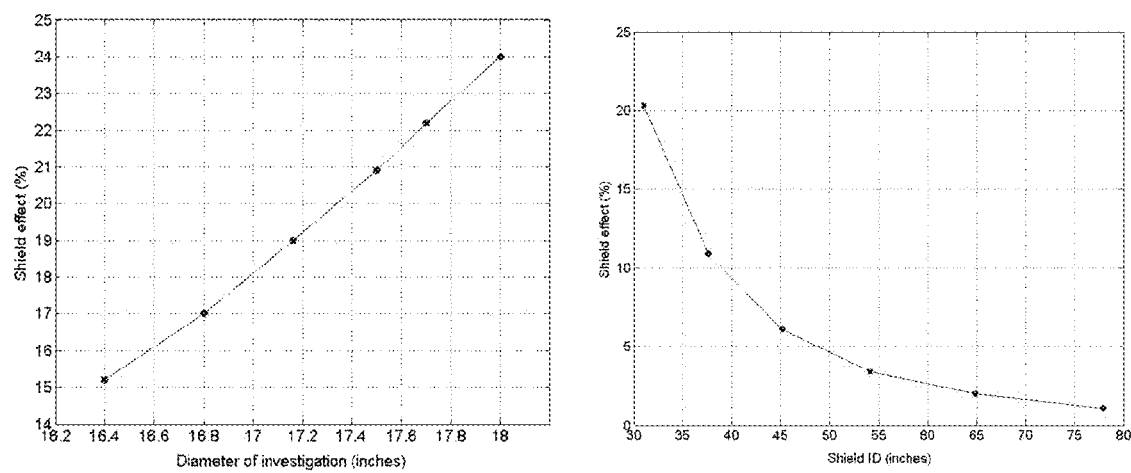
FIG. 3 is a series of graphs that show the dependence of the shield effect on the diameter of investigation and the shield diameter.

The shield effect, as discussed above, strongly depends on the tool DOI and the shield diameter (FIG. 3). Since the DOI may vary from tool to tool, the shield effect also changes for different tools thus making the correction cumbersome. FIG. 3 also shows that the shield effect decreases as the shield diameter is increased but in order to achieve the shield effect below 1% the diameter of the shield should be very large (more than 6 feet (approximately 2 meters)). The large size of the calibration shield makes calibration measurements very inconvenient.

Figure 4:
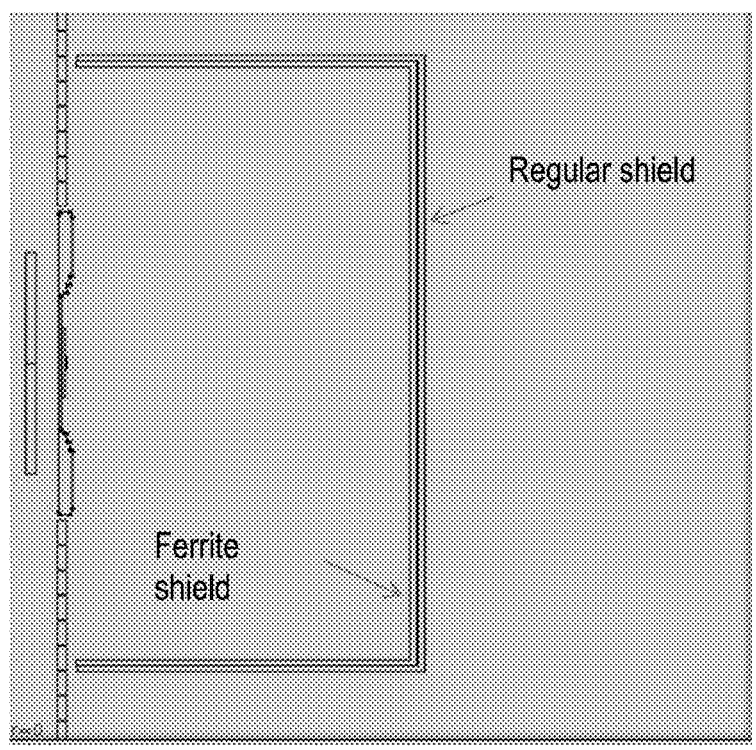
FIG. 4 is a side view of a composite shield for shielding electromagnetic noise from the environment, wherein a regular metallic shield is placed on the outside and a ferrite shield is placed on the inside of the tool.

The novel shield design described here comprises of two parts: a first metallic shield which serves to shield the NMR antenna from noise and a second ferrite shield which serves to eliminate eddy currents in the metallic shield (FIG. 4). The second ferrite shield can be made of any high magnetic permeability nonconductive material with low magnetoacoustic ringing (i.e. iron powder). This design practically eliminates the shield effect while keeping the size of the shield small to be convenient in operation.

Referring to FIG. 4, a composite shield is illustrated wherein a regular metallic shield is placed on the outside and a ferrite shield is placed on the inside. Such a configuration provides for the reduction of eddy currents in the first metallic shield.

Figure 5:
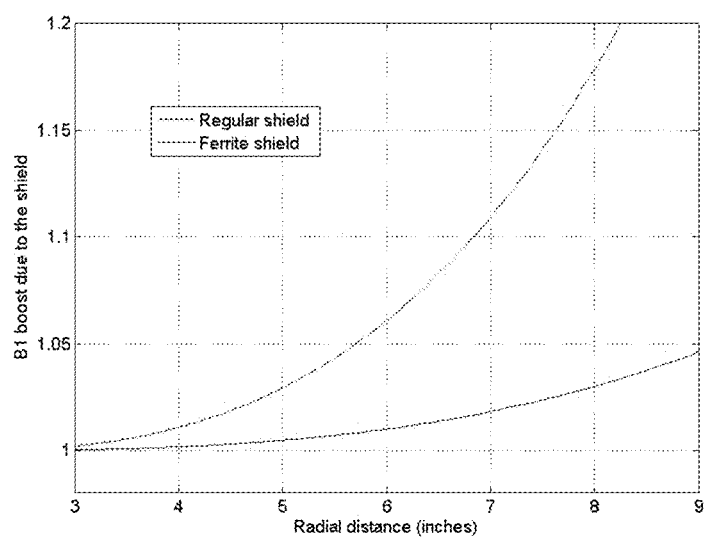
FIG. 5 is a graph of the B1 magnetic field strength boost vs. radial distance for a regular shield and a composite shield.

Referring to FIG. 5., the enhancement of the B1 field with a regular shield (red) and a composite shield (blue) is illustrated. The shield effect is significantly less for the composite shield (less than 1% for the radial distance of 5" which corresponds to DOI=10"). As a result, the composite shield produces a significantly less shield effect, thereby increasing the overall accuracy of the NMR measurement downhole.

As illustrated above, the eddy currents in the composite shield are greatly suppressed because the stray RF magnetic field is concentrated in the ferrite shield thus avoiding the metallic shield. Ferrite material with magnetic permeability of p=100 and thickness of 0.1" limits the shield effect to less than 1% with about 2 feet diameter shield (FIG. 5).

In one example embodiment, the ferrite shield doesn't necessarily have to cover the whole area of the metallic shield, in fact a partial coverage maybe beneficial for several reasons: to limit the weight and to eliminate the small effect of the ferrite shield on the constant magnetic field B0. Optimization of the ferrite and metallic shield sizes in the composite design will depend on the exact tool characteristics (tool diameter, magnet spacing, DOI).

Figure 6:
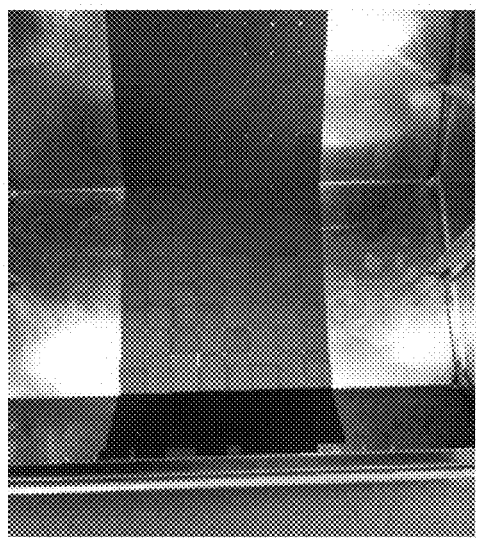
FIG. 6 is a side elevation of a construction of the composite shield of FIG. 1.

Referring to FIG. 6, in another example embodiment, the composite shield may be constructed by gluing the ferrite tiles or ferrite film to the regular shield. Although FIG. 6 describes gluing of the ferrite tiles or ferrite film to the shield, other mechanical and chemical fastening methods may be used.

In one non-limiting example embodiment, an arrangement for shielding an NMR tool from electromagnetic noise is disclosed having a nuclear magnetic resonance tool configured to send and receive signals, a first shield configured around a nuclear magnetic resonance antenna of the nuclear magnetic resonance tool and a second shield configured to reduce the effects of eddy currents in the first shield In another non-limiting example embodiment, an arrangement for shielding an electromagnetic noise is disclosed wherein the second shield is configured from a ferrite material.

In another non-limiting example embodiment, an arrangement for shielding an electromagnetic noise is disclosed, wherein the ferrite material is a high magnetic permeability nonconductive material.

In another non-limiting example embodiment, the arrangement for shielding an electromagnetic noise is disclosed wherein the ferrite material has a low magnetoacoustic ringing.

In another non-limiting example embodiment, the arrangement for shielding an electromagnetic noise is disclosed wherein the second shield is configured from an iron powder.

In another non-limiting example embodiment, the arrangement for shielding an electromagnetic noise is disclosed wherein the first shield is placed to an exterior side of the second shield.

In another non-limiting example embodiment the arrangement for shielding a noise is disclosed wherein the first shield is placed to an exterior side of the second shield for only a portion of the surface area of the second shield.

In another non-limiting example embodiment, an arrangement for shielding an electromagnetic noise in a downhole tool is disclosed having a nuclear magnetic resonance tool configured to send and receive signals into a calibration water tank, the tool having a body configured to house components, a first shield configured around a nuclear magnetic resonance antenna of the nuclear magnetic resonance tool and a second shield configured to eliminate eddy currents in the first shield, wherein the second shield is constructed from a ferrite film that is in contact with the first shield.

In another example embodiment, an arrangement for shielding an electromagnetic noise in a downhole tool is disclosed having a nuclear magnetic resonance tool configured to send and receive signals into a calibration water tank, the tool having a body configured to house components, a first shield configured around a nuclear magnetic resonance antenna of the nuclear magnetic resonance tool and a second shield configured to eliminate eddy currents in the first shield, wherein the second shield is constructed from a ferrite film that is in contact with the first shield.

In another example embodiment, the arrangement may be constructed wherein the second shield is glued to the first shield.

In one example embodiment, the arrangement may be constructed wherein the second shield is glued to the first shield.

Certain embodiments and features may have been described using a set of numerical upper limits and a set of numerical lower limits. It should be appreciated that ranges including the combination of any two values, e.g., the combination of any lower value with any upper value, the combination of any two lower values, or the combination of any two upper values are contemplated. Certain lower limits, upper limits and ranges may appear in one or more claims below. Numerical values are "about" or "approximately" the indicated value, and take into account experimental error, tolerances in manufacturing or operational processes, and other variations that would be expected by a person having ordinary skill in the art.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include other possible embodiments along with the full scope of equivalents to which such claims are entitled. Accordingly, the claims are not limited by the disclosure.

What is claimed is:

1. An arrangement for shielding an NMR tool from electromagnetic noise, comprising:
   a nuclear magnetic resonance (NMR) tool configured to send and receive signals, the NMR tool having an NMR antenna;
   a planar first shield positioned around the NMR antenna; and
   a second shield configured to reduce the effects of eddy currents in the first shield, wherein the second shield is formed of a portion of a ferrite material, the portion affixed to an inner surface of the first shield.

2. The arrangement for shielding an electromagnetic noise according to claim 1, wherein the second shield is configured from a non-conductive high-magnetic permeability material.

3. The arrangement for shielding an electromagnetic noise according to claim 1, wherein the second shield ferrite material comprises an iron powder.

4. The arrangement for shielding an electromagnetic noise according to claim 1, wherein the second shield comprises a sheet or a film.

5. The arrangement for shielding an electromagnetic noise according to claim 1, wherein the ferrite material has a magnetic permeability of at least 100 and at least a thickness of 0.1 inches.

6. The arrangement for shielding an electromagnetic noise according to claim 1, wherein the portion of the ferrite material comprises tiles affixed to the inner surface of the first shield.

7. The arrangement for shielding an electromagnetic noise according to claim 1, wherein the second shield is positioned interiorly to the first shield relative to the NMR tool.

8. The arrangement for shielding an electromagnetic noise according to claim 1, wherein the ferrite material has a low magneto-acoustic ringing.

9. An arrangement for shielding circuitry in a downhole tool from electromagnetic noise, comprising:
   a nuclear magnetic resonance tool configured to send and receive signals;
   a planar first shield configured around a nuclear magnetic resonance antenna of the nuclear magnetic resonance tool; and
   a second shield configured to eliminate eddy currents in the first shield, wherein the second shield is constructed from a portion of ferrite material that is in contact with an inner surface of the first shield.

10. The arrangement according to claim 9, wherein the second shield is one of glued and affixed to the first shield.

11. The arrangement according to claim 9, wherein the ferrite material has a low magneto-acoustic ringing.

* * * * *